United States Patent
Machida et al.

(10) Patent No.: US 6,541,662 B2
(45) Date of Patent: Apr. 1, 2003

(54) PROCESS FOR PRODUCING A HYDROGENATION PRODUCT OF AN AROMATIC CARBOXYLIC ACID

(75) Inventors: Hiroshi Machida, Okayama (JP); Ko Kedo, Okayama (JP); Fumiya Zaima, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/021,430

(22) Filed: Dec. 19, 2001

(65) Prior Publication Data

US 2002/0115884 A1 Aug. 22, 2002

(30) Foreign Application Priority Data

Dec. 26, 2000 (JP) .......................... 2000-394204

(51) Int. Cl.[7] .............................. C07C 61/09
(52) U.S. Cl. ...................................... 562/509
(58) Field of Search ..................... 562/501, 509; 568/435, 735, 801

(56) References Cited

FOREIGN PATENT DOCUMENTS

| GB | 353373 | * | 1/1930 |
| JP | 014942 | * | 1/1987 |
| JP | 7082211 | * | 3/1995 |
| JP | 029529 | * | 2/1999 |

OTHER PUBLICATIONS

Holderich, W.F. et al, Applied Catalysis A: General (1999), 184 (2) 257–264.*
Yokoyama, T et al; Studies in Surface Science and Catalysis (1994), 90(Acid–Base Catalysis II), 47–58.*

* cited by examiner

Primary Examiner—Paul J. Killos
(74) Attorney, Agent, or Firm—Antonelli, Terry, Stout & Kraus, LLP

(57) ABSTRACT

A process for producing a hydrogenation product of aromatic carboxylic acid which comprises continuously producing the hydrogenation product of aromatic carboxylic acid by hydrogenating an aromatic carboxylic acid having a melting point of 250° C. or higher in a solvent in the presence of a solid catalyst, wherein the hydrogenation is conducted in a condition such that substantially the entire amount of the aromatic carboxylic acid of a raw material is dissolved in the solvent by recycling a portion of a reaction liquid taken out of a reactor into the reactor.

An aromatic carboxylic acid having a high melting point and hardly soluble in solvents can be hydrogenated at a suitable reaction temperature in accordance with a continuous process without using a great amount of a solvent and the reaction product of the object compound can be produced very efficiently.

12 Claims, 1 Drawing Sheet

PROCESS FOR PRODUCING A HYDROGENATION PRODUCT OF AN AROMATIC CARBOXYLIC ACID

BACKGROUND OF THE INVENTION

1. Field of the Invention

The present invention relates to a process for continuously producing a hydrogenation product of an aromatic carboxylic acid having a high melting point and hardly soluble in solvents in the presence of a solid catalyst.

2. Description of the Prior Art

In general, aromatic carboxylic acids and, in particular, aromatic dicarboxylic acids have high melting points and small solubilities in various solvents. On the other hand, the reaction for producing cyclohexanedicarboxylic acids and cyclohexanedimethanols such as 1,4-cyclohexanedicarboxylic acid, 1,3-cyclohexanedicarboxylic acid, 1,4-cyclohexanedimethanol and 1,3-cyclohexanedimethanol from aromatic dicarboxylic acids used as the raw material such as terephthalic acid or isophthalic acid by bringing the raw material into contact with hydrogen is, in general, conducted in a solvent in the presence of a solid catalyst.

Heretofore, in many cases, the above reaction is conducted in accordance with a batch process in which the reaction is conducted at a specific temperature after a raw material and a catalyst are placed into a reactor in combination with a solvent and the obtained reaction product is taken out of the reactor.

For example, a process for producing 1,4-cyclohexanedicarboxylic acid comprising forming 1,4-cyclohexanedicarboxylic acid by treating terephthalic acid with hydrogen at a temperature of 110° C. or higher and 180° C. or lower using water as the solvent in the presence of a catalyst containing palladium and ruthenium and treating the obtained reaction liquid by solid-liquid separation at a temperature in a specific range is described in Japanese Patent Application Laid-Open No. Showa 58(1983)-198439. Although it is described that the process can be conducted in accordance with any of the batch process, the semi-continuous process and the continuous process (lines 15 and 16 at the upper right side of page 3), the batch process of the reaction alone is shown in the examples and no descriptions can be found on the continuous process of the reaction.

A process for producing 1,4-cyclohexanedimethanol by hydrogenation of terephthalic acid in an aqueous medium in the presence of a catalyst containing ruthenium and tin as the components is described in Japanese Patent Application Laid-Open No. 2000-7596. Although it is described that the process can be conducted in accordance with any of the continuous process and the batch process (lines 2 and 3 at the right side of page 3), the batch process of the reaction alone is shown in the examples and no specific descriptions can be found on the continuous process of the reaction.

The reaction in accordance with the batch process has a problem in that the time is consumed ineffectively for procedures which substantially do not contribute to the reaction such as placing raw materials, elevating the temperature to the reaction temperature and taking out the reaction product and the productivity of the reactor is poor. The batch process has a further problem in that, when a catalyst is used repeatedly, separation of the catalyst and the reaction product takes time and energy and the activity of the catalyst decreases rather rapidly due to a change in the temperature.

Therefore, it is desirable that the hydrogenation of an aromatic carboxylic acid is conducted in accordance with the continuous process. As the process for continuously hydrogenating an aromatic carboxylic acid, a process in which an aromatic carboxylic acid is dissolved in water in the form of a salt of an alkali metal and supplied to a fixed bed reactor packed with a catalyst (Japanese Patent Application (as a national phase under PCT) Laid-Open No. Heisei 7(1995)-507041) and a process in which a dialkyl ester of terephthalic acid is used as the raw material for the hydrogenation (Japanese Patent Application Laid-Open No. Heisei 10(1998)-45646) have been known. In these processes, the aromatic dicarboxylic acid is continuously hydrogenated after being converted into a compound having a greater solubility or a lower melting point.

However, the above processes has problems in that additional steps are required in the production process to convert the aromatic carboxylic acid into a compound having a greater solubility or a lower melting point and that auxiliary materials such as an alkali metal compound or an alkyl alcohol have to be used. Therefore, a process for directly hydrogenating an aromatic carboxylic acid in accordance with a continuous process has been desired.

Since ordinary organic compounds have greater solubilities at elevated temperatures, the reaction may be conducted at a higher temperature so that a sufficient solubility can be obtained. However, the reaction at a high temperature has problems in that the yield of the object compound decreases due to decomposition of the raw material and the reaction product and an increase in the amount of byproducts and that the activity of the catalyst decreases rapidly.

For example, when a cyclohexanedicarboxylic acid or a cyclohexane-dimethanol is produced by bringing terephthalic acid or isophthalic acid into contact with hydrogen using water as the solvent, the reaction conducted at a temperature at which the above benzenedicarboxylic acid can be completely dissolved into an industrially suitable amount of water, which is, specifically, a temperature exceeding 200° C., results in a decrease in the yield of the reaction and deterioration in the purity of the reaction product due to decomposition of the raw material and excessive hydrogenation.

SUMMARY OF THE INVENTION

The present invention has, under the above circumstances, an object of providing a process for efficiently producing a hydrogenation product of aromatic carboxylic acid of the object compound by hydrogenation in accordance with a continuous process in the presence of a solid catalyst using as the raw material an aromatic carboxylic acid having a high melting point and a low solubility in solvents, which can hardly be brought into an efficient reaction in accordance with conventional processes.

As the result of intensive studies by the present inventors on the process for efficiently conducting hydrogenation of the above aromatic carboxylic acid in accordance with a continuous process, it was found that the continuous reaction could be conducted at the most suitable reaction temperature in a fixed bed reactor when the reaction liquid was used at least as a portion of the solvent for dissolving the raw material by recycling the reaction liquid and the inside of the reactor was brought to a condition such that substantially the entire amount of the raw material was dissolved. The present invention has been made based on the knowledge.

The present invention provides a process for producing a hydrogenation product of aromatic carboxylic acid which comprises continuously producing the hydrogenation product of aromatic carboxylic acid by hydrogenating an aromatic carboxylic acid having a melting point of 250° C. or higher in a solvent in a presence of a solid catalyst, wherein the hydrogenation is conducted in a condition such that substantially an entire amount of the aromatic carboxylic acid of a raw material is dissolved in the solvent by recycling a portion of a reaction liquid taken out of a reactor into the reactor.

BRIEF DESCRIPTION OF THE DRAWINGS

In FIGS. 1 and 2, 1 means a tank for preparing a slurry of a raw material, 2 means a mixing tank with stirring, 3 means a fixed bed catalytic reactor, 4 means a receiving tank for a reaction product, 5 means a second reactor, 6 means a static mixer, 7 means a catalytic reactor of the stirred tank type and 8 means an apparatus for separation of a catalyst.

DESCRIPTION OF THE PREFERRED EMBODIMENTS

Figure 1:
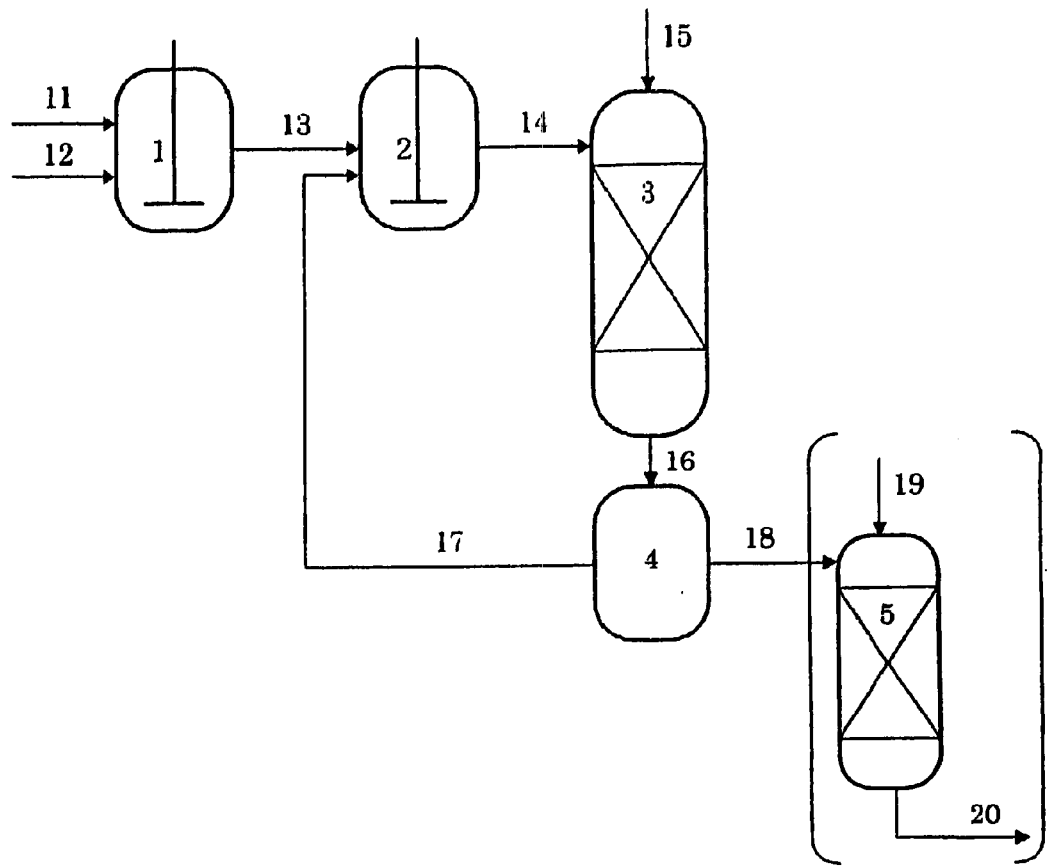
FIG. 1 shows a flow diagram of the process of the present invention in which a fixed bed catalytic reactor is used.

The raw material for producing the hydrogenation product of aromatic carboxylic acid in accordance with the process of the present invention is an aromatic carboxylic acid and preferably an aromatic dicarboxylic acid having a melting point of 250° C. or higher. Specific examples of the aromatic carboxylic acid include terephthalic acid, isophthalic acid, 2,6-naphthalenedicarboxylic acid and 4,4'-biphenyl-dicarboxylic acid. In the present invention, the aromatic carboxylic acid may be used singly or in combination of two or more.

The above aromatic dicarboxylic acids have small solubilities in water and various types of organic solvents. The solubility in water is shown in Table 1.

TABLE 1

| Solubility in water (g/100 g · water) | Temperature | |
|---|---|---|
| | 150° C. | 200° C. |
| Terephthalic acid | 0.25 | 1.7 |
| Isophthalic acid | 2.7 | 24.2 |
| 2,6-naphthalenedicarboxylic acid | 0.03 | 0.21 |
| 4,4'-biphenyldicarboxylic acid | 0.01 | 0.04 |

The reaction conducted in the present invention is hydrogenation using the above raw material in the presence of a solid catalyst. Specifically, it is the reaction in which the aromatic carboxylic acid is. brought into contact with hydrogen gas in the presence of a solid catalyst and the carboxyl group at the aromatic ring or the side chain of the aromatic carboxylic acid is hydrogenated.

Examples of the hydrogenation product of an aromatic carboxylic acid obtained by the above reaction (referred to as the reaction product, hereinafter) include hydrogenation products of the aromatic carboxylic acid in which the aromatic ring alone has been hydrogenated into a group such as cyclohexyl group, tetrahydronaphthyl group and decahydro-naphthyl group, compounds in which at least one of carboxyl groups as the side groups has been hydrogenated into formyl group, hydroxymethyl group or methyl group and compounds in which the aromatic ring and the side chains have both been hydrogenated.

Examples of the reaction product obtained by the reaction using terephthalic acid, isophthalic acid, 2,6-naphthalenedicarboxylic acid or 4,4'-biphenyldicarboxylic acid as the raw material include compounds represented by the following general formulae (1) to (6):

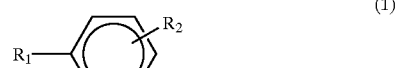

(1)

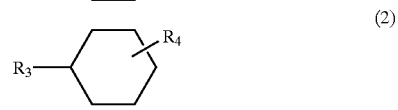

(2)

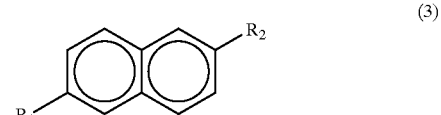

(3)

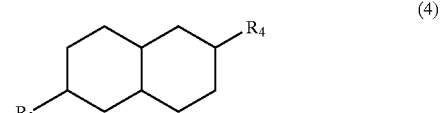

(4)

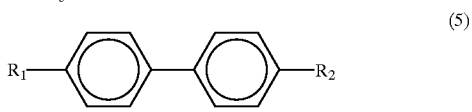

(5)

(6)

wherein $R_1$, $R_2$, $R_3$ and $R_4$ each represent COOH, CHO, $CH_2OH$ or $CH_3$, $R_1$ and $R_2$ are not COOH or $CH_3$ at the same time and $R_3$ and $R_4$ are not $CH_3$ at the same time Since these compounds have greater solubilities in solvents or lower melting points than the aromatic carboxylic acids of the raw material, these compounds can be taken out of the reactor as a solution having a high concentration or as a melt.

The solvent used in the present invention is not particularly limited as long as the solvent can be used for the object of the present invention. However, solvents having a great reactivity to the aromatic carboxylic acid of the raw material such as amines, dimethylformamide and lower aliphatic alcohols cannot be used. When the reaction product has a melting point lower than the temperature of the reaction, the reaction product can be used as the solvent.

In the present invention, the hydrogenation is conducted continuously using a solid catalyst. The solid catalyst is not particularly limited as long as the solid catalyst is suitable for the hydrogenation described above. When a cyclohexanedicarboxylic acid is produced by hydrogenation of the aromatic ring of an aromatic dicarboxylic acid, examples of the catalyst include catalysts containing a metal such as palladium and ruthenium supported on activated carbon.

As the continuous reactor used in the present invention, a fixed bed catalytic reactor 3 shown in FIG. 1 is most preferable. In this type of the reactor, when the aromatic carboxylic acid of the raw material is not completely dissolved within the reactor and solid substances are left remaining, clogging takes place and it is difficult that a stable operation for a long time is achieved. Therefore, it is necessary that substantially the entire amount of the aromatic carboxylic acid of the raw material is dissolved within the reactor. It is preferable that, when the reaction liquid is recycled, the reaction liquid is supplied in a condition such that the aromatic carboxylic acid of the raw material is completely dissolved at the inlet of the reactor.

In FIG. 1, an aromatic carboxylic acid 11 of the raw material and a solvent 12 in a suitable amount are mixed in a tank for preparing a slurry of a raw material 1 and a slurry of the raw material 13 is prepared. The amount of the solvent used in the preparation is adjusted to an amount satisfying conditions such that the aromatic carboxylic acid of the raw material is not completely dissolved but forms a slurry and that the amount is at least the amount necessary for completely dissolving the reaction product in the reactor when the reaction liquid is recycled. However, an excessive amount of the solvent is not preferable since separation of the reaction product and the solvent becomes difficult. Specifically, the amount of the solvent in the reactor is 20 parts by weight or less, preferably 10 parts by weight or less and more preferably 5 parts by weight or less per 1 part by weight of the reaction product. In the present invention, the amount of the fresh solvent can be decreased since the reaction liquid containing the solvent is recycled. When the reaction liquid itself is used as the solvent, the reaction liquid is used as the solvent in an amount such that a slurry containing the aromatic carboxylic acid 11 of the raw material is formed by using the recycled reaction liquid 17 and can be supplied continuously to a mixing tank with stirring 2 or directly to the reactor 3.

After being mixed with the solvent, the aromatic carboxyhic acid of the raw material is supplied to a mixing tank with stirring 2 or directly to the reactor 3 in the condition of a slurry. The slurry of the raw material 13 is mixed in the mixing tank with stirring 2 or the reactor 3 with a recycled reaction liquid 17 which is separated in a receiving tank for the reaction product 4 from the reaction liquid 16 taken out of the reactor. The concentration of the slurry is adjusted so that the entire amount of the raw material is dissolved into the solvent containing the reaction product at the temperature condition in the reactor. When the slurry of the raw material 13 and the recycled reaction liquid 17 are mixed together before being supplied to the reactor 3, the mixing tank with stirring 2 as shown in FIG. 1 or a static mixer may be used.

In the fixed bed catalytic reactor, the aromatic carboxylic acid of the raw material is brought into contact with the catalyst held at the fixed bed and hydrogen and the hydrogenation takes place. Hydrogen is supplied continuously from the line 15 to the reactor 3. Hydrogen is supplied to any of (i) the reactor 3, (ii) the mixing tank with stirring 2 in which the slurry containing the aromatic carboxylic acid of the raw material and the recycled reaction liquid are mixed together and (iii) the line for supplying the raw material 14 through which the solution of the raw material is supplied to the reactor. In general, the reaction rate in the hydrogenation of an aromatic carboxylic acid is affected by the amount of hydrogen gas dissolved in the reaction liquid. In the process of the present invention, since the amount of the solution relative to the amount of the aromatic carboxylic acid of the raw material is great due to the recycling of the reaction liquid, the amount of dissolved hydrogen can be increased. Therefore, the reaction can be conducted advantageously.

The process of the present invention is characterized in that the reaction liquid continuously taken out of the reactor is recycled. Since the recycled reaction liquid 17 can be used for the recycling while the temperature and the pressure are kept close to those in the reactor, the process is advantageous for saving power and heat energy. In general, the hydrogenation is an exothermic reaction. Therefore, the reaction liquid may be cooled by passing the recycled reaction liquid through a heat exchanger.

The reaction liquid taken out of the reactor 18 which is not recycled is transferred to the next step and separated into the reaction product and the solvent. Where desired, the reaction liquid may be supplied to a second reactor 5 before being subjected to the separation and brought into reaction with hydrogen supplied from a line 19 so that the yield of the object product is increased. For the separation into the reaction product and the solvent, any conventional process used in processes for producing chemical products can be used. Examples of such process include (A) a process in which the solvent is removed by distillation by heating the reaction liquid and the reaction product is recovered and (B) a process in which crystals of the reaction product are separated by cooling the reaction liquid and recovered by a solid-liquid separation machine. In the process of the present invention, the separation of the reaction product can be advantageously performed since the concentration of the reaction product in the reaction liquid can be increased.

Figure 2:
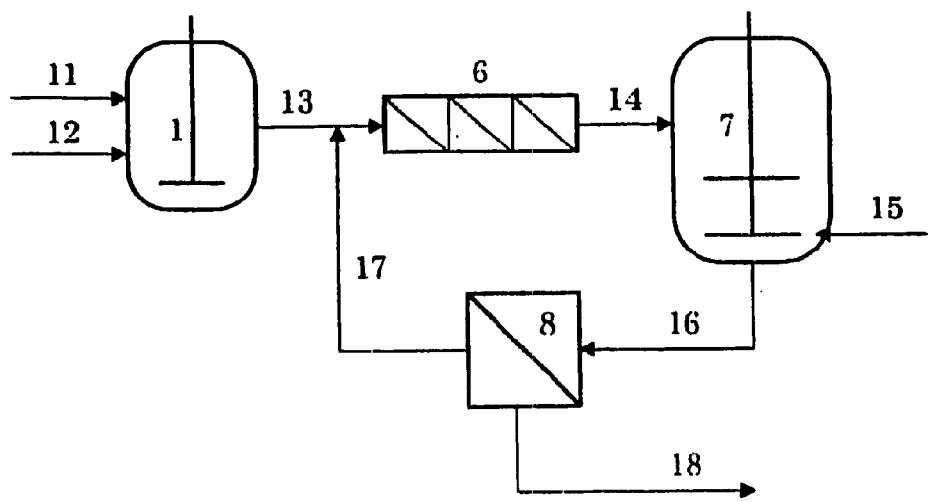
FIG. 2 shows a flow diagram of the process of the present invention in which a tank reactor is used.

In the present invention, as another embodiment, a catalytic reactor of the stirred tank type 7 shown in FIG. 2 is used and hydrogen from a line 15 is brought into the reaction while the solid catalyst is dispersed in the reaction liquid by stirring. In this embodiment, the hydrogenation is conducted in a condition such that the solid catalyst is dispersed in the solvent in the reactor. The reaction liquid taken out of the reactor is separated into a portion which contains substantially no amount of the catalyst and a portion which contains substantially the entire amount of the catalyst. The portion of the reaction liquid which contains substantially the entire amount of the catalyst is mixed with the aromatic carboxylic acid of the raw material and the resultant mixture is recycled to the reactor. As the apparatus for separation of a catalyst 8 which is used for separating the reaction liquid taken out of the reactor into a portion which contains substantially no amount. of the catalyst and a portion which contains substantially the entire amount of the catalyst, any apparatus such as a cyclone, a centrifuge and a filter can be used. The separated recycled reaction liquid 17 containing the solid catalyst is mixed with the slurry of the raw material 13 as shown in FIG. 2 and recycled to the catalytic reactor of a stirred tank type 7. The recycled reaction liquid 17 may be recycled directly to the catalytic reactor of a stirred tank type 7. In the process of the present invention, the reaction is conducted in the reactor in the condition such that the raw material is completely dissolved. Therefore, it is sufficient that a portion of the reaction liquid is treated for the separation in the apparatus for separation of a catalyst 8 and the load applied to the apparatus for separation of a catalyst can be decreased from that required for conducting the reaction of the raw material in the condition of a slurry.

In the process shown in FIG. 2, the reaction liquid 18 taken out of the reactor of the stirred tank type 7 and treated for removal of the catalyst is transferred to the next step and separated into the reaction product and the solvent in the same manner as that in the process using the fixed bed catalytic reactor shown in FIG. 1. Where desired, the reaction liquid may be supplied to a second reactor before being subjected to the separation and brought into the reaction with hydrogen so that the yield of the object product is increased.

In accordance with the process of the present invention, the reaction of the aromatic dicarboxylic acid having a high melting point and hardly soluble in solvents can be reacted in accordance with a continuous process at a suitable temperature without using a great amount of a solvent. Therefore, the object reaction product can be produced very efficiently.

EXAMPLES

The present invention will be described specifically with reference to examples in the following. However, the present invention is not limited to the examples.

Example 1

The synthesis of 1,3-cyclohexanedicarboxylic acid by hydrogenation of isophthalic acid was conducted in accordance with a process having a flow scheme approximately the same as that shown in FIG. 1. A second reactor was not used.

A fixed bed catalytic reactor having an inner diameter of 20 mm and a length of 800 mm was used as the reactor. The reactor was packed with 200 ml of a 0.5% palladium catalyst supported on activated carbon (manufactured by NE CHEMCAT Company). A receiving tank for a reaction product was disposed at a lower portion of the reactor. A flow scheme was formed in a manner such that a portion of the reaction product was taken out of the reaction system and the remaining portion was mixed with a slurry of the raw material using a static mixer and recycled to an inlet of the reactor by a pump.

The apparatus was heated by circulating water by a pump for circulating the reaction liquid and the temperature was adjusted at 170° C. Nitrogen was supplied from a line 15 disposed at an upper portion of the reactor and the pressure inside the reactor was adjusted at 3 MPa.

In a tank for preparing a slurry of a raw material, isophthalic acid and water were mixed in amounts such that the ratio of the amounts by weight was 1 to 3. The flow rate of the reaction liquid was adjusted at 600 ml/hour and the supply of hydrogen gas from the line 15 was started at a flow rate of 100 NL/hour. Then, the pump for supplying the raw material was activated and the slurry of the raw material was supplied at a flow rate of 200 ml/hour. The hydrogenation was conducted continuously for about 7 hours while the reaction temperature was adjusted at 170° C. and the reaction pressure was adjusted at 3 MPa. The reaction liquid was intermittently taken out of the receiving tank for the reaction product.

The results of the reaction obtained from the compositions of the reaction liquid and the off gas which were taken out about 6 hours after the start of the reaction were as follows: the conversion of isophthalic acid: 99.3% by mole; and the yield of 1,3-cyclohexanedicarboxylic acid: 96.2% by mole.

Comparative Example 1

The reaction was conducted using the same apparatus as those used in Example 1 except that the reaction liquid was not recycled and the slurry of the raw material was supplied directly to the reactor.

Isophthalic acid and water were mixed in the tank for preparing a slurry of a raw material in the same amounts as those in Example 1, i.e., in amounts such that the ratio of the amounts by weight was 1 to 3. The raw material was preheated at 210° C. so that the entire amount was dissolved into water and supplied to the reactor. The hydrogenation was conducted in the same manner as that in Example 1 except that the reaction temperature was 210° C. and the reaction pressure was 4 MPa.

The results of the reaction obtained from the compositions of the reaction liquid and the off gas which were taken out about 6 hours after the start of the reaction were as follows: the conversion of isophthalic acid: 99.8% by mole; and the yield of 1,3-cyclohexanedicarboxylic acid: 90.4% by mole.

When the composition was compared with that in Example 1, impurities such as cyclohexane and methylcyclohexane were formed in greater amounts.

Example 2

The hydrogenation of terephthalic acid of the raw material was conducted using the same apparatus as that used in Example 1. The hydrogenation was conducted under the same conditions as those in Example 1 except that terephthalic acid and water were mixed in amounts such that the ratio of the amounts by weight was 1 to 4 in the tank for preparing a slurry of a raw material, the flow rate of the slurry of the raw material was 150 ml/hour, the flow rate of recycled reaction liquid was 1,800 ml/hour, the flow rate of the supply of hydrogen was 80 NL/hour, the reaction temperature was 200° C. and the reaction pressure was 4 MPa.

The results of the reaction obtained from the compositions of the reaction liquid and the off gas which were taken out about 6 hours after the start of the reaction were as follows: the conversion of terephthalic acid: 99.5% by mole; and the yield of 1,4-cyclohexanedicarboxylic acid: 94.7% by mole.

Example 3

The hydrogenation was conducted under the same conditions as those in Example 2 except that. the reaction temperature was 190° C. Although the solubility of terephthalic acid in water showed that terephthalic acid of the raw material was not soluble completely, the reaction could be conducted for about 7 hours without any problem. It is estimated that the solubility of terephthalic acid was increased by recycling the reaction liquid and terephthalic acid was completely dissolved.

The results of the reaction obtained from the compositions of the reaction liquid and the off gas which were taken out about 6 hours after the start of the reaction were as follows: the conversion of terephthaiic acid: 98.9% by mole; the yield of 1,4-cyclohexanedicarboxylic acid: 95.6% by mole; and the fraction of formation of 1,4-cyclohexanedimethanol: 0.1% by mole.

Comparative Example 2

The hydrogenation was conducted using terephthalic acid as the raw material using the same apparatus as those used in Comparative Example 1. Terephthalic acid and water were mixed in the tank for preparing a slurry of a raw material in the same amounts as those in Example 2, i.e., in amounts such that the ratio of the amounts by weight was 1 to 4. The raw material was preheated at 270° C. so that the entire amount was dissolved into water and supplied to the reactor. The hydrogenation was conducted in the same manner as those in Example 2 except that the reaction temperature was 270° C. and the reaction pressure was 8 MPa.

The results of the reaction obtained from the compositions of the which were taken out about 6 hours after the start of the reaction were as follows: the conversion of terephthalic acid: 100% by mole; and the yield of 1,4-cyclohexanedicarboxylic: 82.5% by mole. When the composition was compared with that in Example 1, impurities such as cyclohexane and methylcyclohexane were formed in much greater amounts.

Example 4 the reation of synthesizing 1,4-cyclohexanedicarboxylic acid by hydrogenation of terephthalic acid was conducted in accordance with the same flow scheme as that shown in FIG. 2.

An autoclave of the stirring type having an inner volume of about 10 liters and equipped with a tube for blowing a gas into a liquid was used as the reactor. CP FILTER (a trade name; manufactured by ISHIKAWAJIMA HARIMA JUKO-GYO Co., Ltd.) was used as the apparatus for separation of the catalyst. This filter is a filtration apparatus in which a liquid of a raw material is circulated by a pump and the liquid of a raw material is continuously filtered with a filter element made of ceramics and separated into a filtrate and a liquid containing concentrated solid substances. The flow scheme was constructed in a manner such that the filtrate was taken out as the solution of the reaction product and the reaction liquid containing the solid catalyst was mixed with the slurry of the raw material by a static mixer and recycled to an inlet of the reactor.

Into the above reactor, 40 g of a 5% palladium catalyst supported on activated carbon in the powder form (manufactured by NE CHEMCAT Company) and 6 liters of water were placed. The resultant mixture was heated at 190° C. and the pressure was adjusted at 4 MPa by supplying nitrogen.

In a tank for preparing a slurry of a raw material, terephthalic acid and water were mixed in amounts such that the. ratio of the amounts by weight was 1 to 4. The flow rate of the recycled reaction liquid was adjusted at 150 liters/hour and the supply of hydrogen gas from a line 15 was started at a flow rate of 500 NL/hour. Then, the pump for supplying the raw material was activated and the slurry of the raw material was supplied at a flow rate of 3 liters/hour. The hydrogenation was conducted continuously for about 7 hours while the reaction temperature was adjusted at 190° C. and the reaction pressure was adjusted at 4 MPa. The reaction liquid was filtered to separate the catalyst and was taken out into the tank for receiving the reaction product in a manner such that the surface of the liquid in the reactor was held at the same position.

The results of the reaction obtained from the compositions of the reaction liquid and the off gas which were taken out about 6 hours after the start of the reaction were as follows: the conversion of terephthalic acid: 98.7% by mole; the yield of 1,4-cyclohexanedicarboxylic acid: 95.8% by mole; and the rate of formation of 1,4-cyclohexanedicarboxylic acid per unit reaction time and unit volume of the reaction: 0.63 mole/(liter-hour).

Comparative Example 3

The reaction of synthesis of 1,4-cyclohexanedicarboxylic acid by hydrogenation of terephthalic acid was conducted in accordance with the batch process using the same reactor as that used in Example 4.

Into the reactor, 1.2 kg of terephthalic acid, 4.8 kg of water and 40 g of a 5% palladium catalyst supported on activated carbon in the powder form (manufactured by NE CHEMCAT Company) were placed. The resultant mixture was heated at 190° C. and the pressure was adjusted at 4 MPa by supplying nitrogen.

The supply of hydrogen was started at a flow rate of 500 NL/hour and continued for 2 hours while the temperature was adjusted at 190° C. and the pressure was adjusted at 4 MPa. After the reaction was completed, the reactor was cooled and the reaction product was taken out.

The results of the reaction obtained by the analysis of the reaction product were as follows: the conversion of terephthalic acid: 96.2% by mole; and the yield of 1,4-cyclohexanedicarboxylic acid: 93.0% by mole; and the average rate of formation of 1,4-cyclohexanedicarboxylic acid per unit reaction time and unit volume of the reaction: 0.56 mole/liter-hour). The conversion of terephthalic acid was smaller than that obtained in accordance with the continuous process and the rate of formation of 1,4-cyclohexanedicarboxylic acid was also smaller than that obtained in accordance with the continuous process even though the reaction was conducted in accordance with the batch process.

Example 5

The hydrogenation of 2,6-naphthalenedicarboxylic acid was conducted using the same reactor as that used in Example 4.

Into the reactor, 100 g of a 5% ruthenium catalyst supported on activated carbon in the powder form (manufactured by NE CHEMCAT Company) and 6 liters of water were placed. The resultant mixture was heated at 180° C. and the pressure was adjusted at 6 MPa by supplying nitrogen.

In the tank for preparing a slurry of a raw material, 2,6-naphthalenedicarboxylic acid and water were mixed in amounts such that the ratio of the amounts by weight was 1 to 5. The flow rate of the recycled reaction liquid was adjusted at 150 liters/hour and the supply of hydrogen gas from the line 15 was started at a flow rate of 500 NL/hour. Then, the pump for supplying the raw material was activated and the slurry of the raw material was supplied at a flow rate of 3 liters/hour. The hydrogenation was conducted continuously for about 7 hours while the reaction temperature was adjusted at 180° C. and the reaction pressure was adjusted at 6 MPa. After the catalyst was separated by filtration, the reaction liquid was taken out into the tank for receiving the reaction product in a manner such that the surface of the liquid in the reactor was held at the same position.

The results of the reaction obtained from the compositions of the reaction liquid and the off gas which were taken out about 6 hours after the start of the reaction were as follows: the conversion of 2,6-naphthalenedicarboxylic acid: 99.3% by mole; the yield of 2,6-decaline-dicarboxylic acid: 92.2% by mole; the yield of 2,6-tetralinedicarboxylic acid: 4.9% by mole; and the rate of formation of 2,6-decalinedicarboxylic acid per unit reaction time and unit volume of the reaction: 0.37 mole/(liter-hour).

Comparative Example 4

The hydrogenation of 2,6-naphthalenedicarboxylic acid was conducted in accordance with the batch process using the same reactor as that used in Example 5.

Into the reactor, 1 kg of 2,6-naphthalenedicarboxylic acid, 5 kg of water and 100 g of a 5% ruthenium catalyst supported on activated carbon in the powder form (manufactured by NE CHEMCAT Company) were placed. The resultant mixture was heated at 180° C. and the pressure was adjusted at 6 MPa by supplying nitrogen.

The supply of hydrogen gas from the line 15 was started at a flow rate of 500 NL/hour and continued for 2 hours while the temperature was adjusted at 180° C. and the pressure was adjusted at 6 MPa. After the reaction was completed, the reactor was cooled and the reaction product was taken out.

The results of the reaction obtained by the analysis of the reaction product were as follows: the conversion of 2,6-naphthalenedicarboxylic acid: 88.3% by mole; the yield of 2,6-decalinedicarboxylic acid: 63.5% by mole; the yield of 2,6-tetralinedicarboxylic acid: 19.2% by mole; and the average rate of formation of 2,6-decalinedicarboxylic acid per unit reaction time and unit volume of the reaction: 0.24 mole/(liter-hour).

What is claimed is:

1. A process for producing a hydrogenation product of aromatic carboxylic acid which comprises continuously producing the hydrogenation product of aromatic carboxylic acid by hydrogenating an aromatic carboxylic acid having a melting point of 250° C. or higher in a solvent in a presence of a solid catalyst, wherein the hydrogenation is conducted in a condition such that substantially an entire amount of the aromatic carboxylic acid of a raw material is dissolved in the solvent by recycling a portion of a reaction liquid taken out of a reactor into the reactor.

2. A process according to claim 1, wherein a slurry is prepared from the aromatic carboxylic acid of a raw material and the solvent and the prepared slurry is supplied continuously to the reactor.

3. A process according to claim 2, wherein the reaction liquid is mixed with the slurry and a resultant mixture is continuously supplied to the reactor.

4. A process according to claim 3, wherein a static mixer is used for mixing the reaction liquid and the slurry.

5. A process according to claim 2, wherein the reaction liquid is mixed with the slurry and a resultant mixture is supplied to the reactor in a condition such that the aromatic carboxylic acid of the raw material is completely dissolved at an inlet of the reactor.

6. A process according to claim 1, wherein the reactor contains the solid catalyst held at a fixed bed.

7. A process according to claim 1, wherein the hydrogenation is conducted in a condition such that the solid catalyst is dispersed in the solvent in the reactor, the reaction liquid taken out of the reactor is separated into a portion which contains substantially no amount of the catalyst and a portion which contains substantially an entire amount of the catalyst, the portion of the reaction liquid which contains substantially an entire amount of the catalyst is mixed with the aromatic carboxylic acid of the raw material and a resultant mixture is recycled to the reactor.

8. A process according to claim 1, wherein a portion of the reaction liquid which is not recycled into the reactor is supplied to a second reactor.

9. A process according to claim 1, wherein the hydrogenation product of the aromatic carboxylic acid as a reaction product is used as the solvent.

10. A process according to claim 1, wherein the aromatic carboxylic acid is an aromatic dicarboxylic acid.

11. A process according to claim 10, wherein the aromatic carboxylic acid is at least one aromatic dicarboxylic acid selected from terephthalic acid, isophthalic acid, 2,6-naphthalenedicarboxylic acid and 4,4'-biphenyldicarboxylic acid.

12. A process according to claim 11, wherein the hydrogenation product of aromatic carboxylic acid is a compound selected from compounds represented by general formulae (1) to (6):

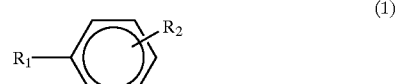

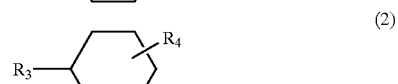

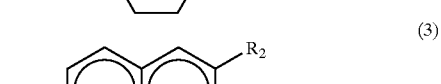

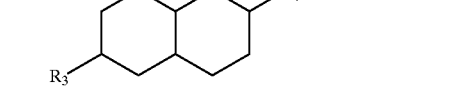

wherein $R_1$, $R_2$, $R_3$ and $R_4$ each represent COOH, CHO, $CH_2OH$, or $CH_3$, $R_1$ and $R_2$ are not COOH or $CH_3$ at the same time and $R_3$ and $R_4$ are not $CH_3$ at the same time.

* * * * *